(12) United States Patent
Jacobson et al.

(10) Patent No.: US 6,417,235 B2
(45) Date of Patent: Jul. 9, 2002

(54) METHOD AND USE OF α-AMINO-β-MERCAPTO-ETHANE DERIVATIVES AS DICARBONYL SCAVENGERS FOR TREATMENT OF CONDITIONS RESULTING FROM PROTEIN, LIPID, AND DNA DAMAGE

(75) Inventors: Elaine L. Jacobson; Myron K. Jacobson; Georg T. Wondrak; Daniel Cervantes Laurean, all of Tucson, AZ (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/836,552

(22) Filed: Apr. 16, 2001

Related U.S. Application Data

(60) Provisional application No. 60/197,216, filed on Apr. 14, 2000.

(51) Int. Cl.[7] .................. A61K 31/13; A61K 31/195
(52) U.S. Cl. ........................... 514/665; 514/562
(58) Field of Search ................... 514/562, 665

(56) References Cited

U.S. PATENT DOCUMENTS

| | | | | |
|---|---|---|---|---|
| 4,731,200 A | * | 3/1988 | Lang et al. | |
| 5,124,356 A | * | 6/1992 | Purcell et al. | |
| 5,126,442 A | * | 6/1992 | Farmer et al. | |
| 5,334,617 A | * | 8/1994 | Ulrich et al. | |
| 5,801,200 A | * | 9/1998 | Bucala et al. | |

OTHER PUBLICATIONS

Database Embase, Abstract No. 1999376124, "Inhibition of nonenzymatic protein glycation and lipid . . . activity", Life Sciences Oct. 1, 1999, 65/18–19, 1991–1993.

Datbase Biosis, Abstract No. 1997:139942, "Strain of Rat Skin at Constant Load Creep . . . Agents", Gerontology, 1976, 23(2), 77–86.

Database CAPLUS, Abstract No. 1988:545412, "In vitro and in vivo protection against phototoxic . . . agents WR–721 and WR–77913", Photochem Photobiol. 1988, 48/2, 235–8.

* cited by examiner

Primary Examiner—William R. A. Jarvis
Assistant Examiner—Vickie Kim
(74) Attorney, Agent, or Firm—Fulbright & Jaworski L.L.P.

(57) ABSTRACT

Methods of inhibiting damage to proteins, lipids, and DNA by the use of penicillamines and other α-amino-β,β-mercapto-β,β-dimethyl-ethane compounds as dicarbonyl scavengers is disclosed.

2 Claims, 19 Drawing Sheets

Nia-201   D,L-PENICILLAMINE
Nia-202   L-PENICILLAMINE
Nia-203   D-PENICILLAMINE
Nia-204   D-PENICILLAMINEDISULFIDE
Nia-205   N,S-ISOPROPYLIDENE-D-PENICILLAMINE

DICARBONYL SCAVENGING ACTIVITY OF d-PENICILLAMINE: RAPID REACTION WITH PHENYLGLYOXAL d-PENILLAMINE (10 mM) AND PHENYLGLYOXAL (20 mM) WERE REACTED AT pH 7.4 (50 mM $KH_2PO_4$) AT ROOM TEMPERATURE. THE REACTION WAS MONITORED BY REVERSE PHASE HPLC (DETECTION AT 254 nm)

REACTION OF D-PENICILLAMINE WITH REACTIVE DICARBONYL COMPOUNDS (e.g. PHENYLGLYOXAL)
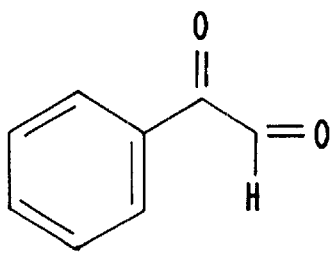
PHENYLGLYOXAL
pH 7.4
37°C
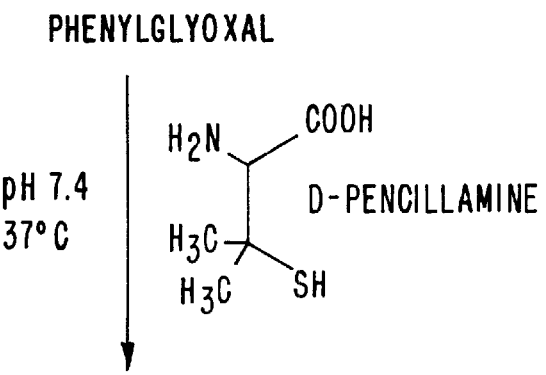
D-PENCILLAMINE
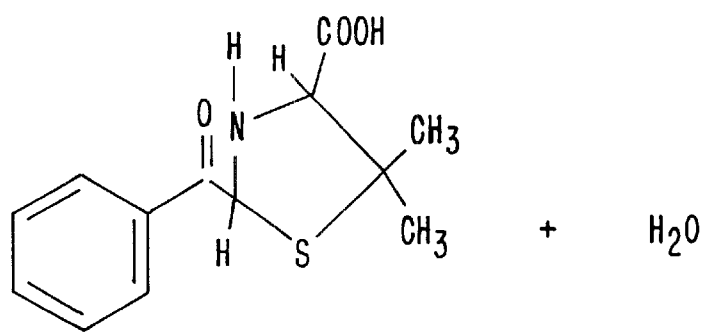   +   $H_2O$
THIAZOLIDINE-DERIVATIVE OF PHENYLGLYOXAL
*FIG. 9*

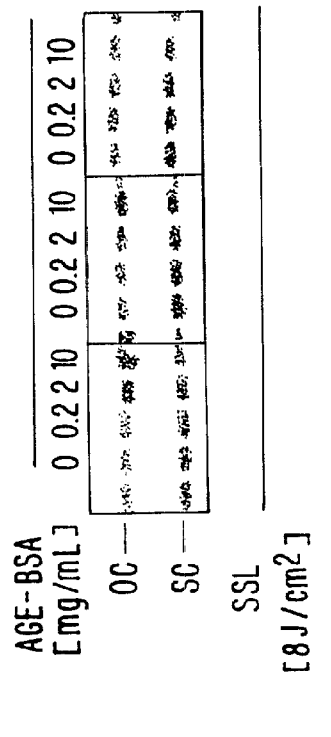

FIG.10D

AGE-BSA PHOTOSENSITIZED CLEAVAGE OF ⌀X-174 DNA. DOSE-DEPENDENT INHIBITION OF AGE-BSA SENSITIZED DNA PHOTOCLEAVAGE BY D-PENICILLAMINE

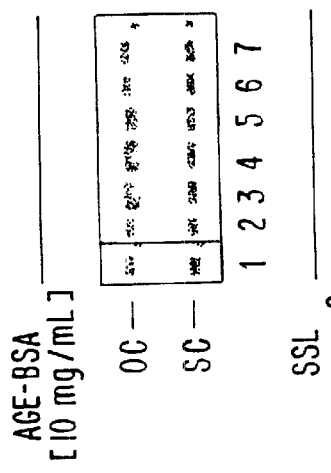

FIG.10C

AGE-BSA PHOTOSENSITIZED CLEAVAGE OF ⌀X-174 DNA. INHIBITION OF AGE-BSA SENSITIZED DNA PHOTOCLEAVAGE UNCLEAVED CONTROL DNA (1), DNA CLEAVAGE SYSTEM+ NaN₃(2), DNA CLEAVAGE SYSTEM+MANNITOL (3), DNA CLEAVAGE SYSTEM + SOD (4), DNA CLEAVAGE SYSTEM + CATALASE (5), DNA CLEAVAGE SYSTEM+ L-CYSTEINE (6), DNA CLEAVAGE SYSTEM+ D-PENICILLAMINE(7)

▼ H1 and ADP-ribose
■ H1 alone
▲ ADP-ribose alone
◆ H1, ADP-ribose + 5 mM aminoguanidine

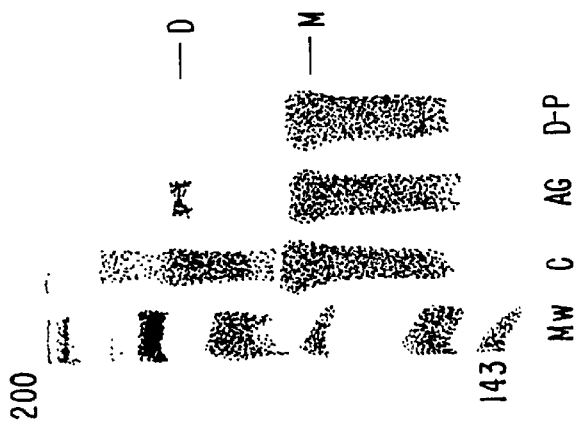

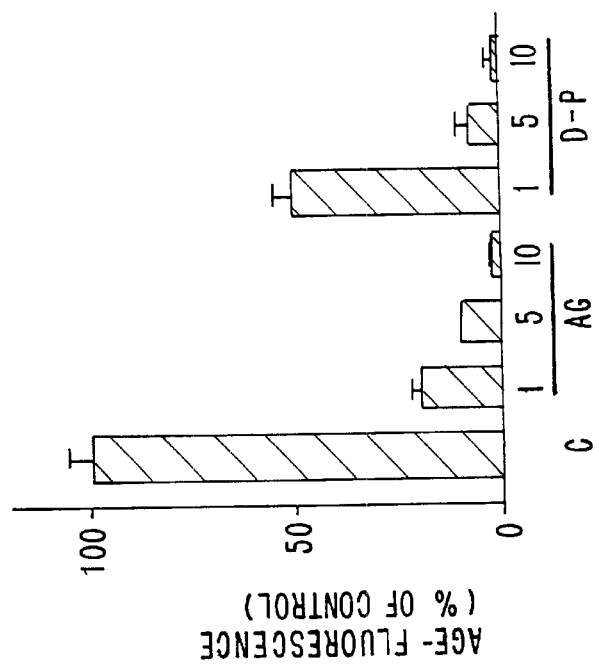

C = control between H1 and ADP-ribose
AG = reaction in presence of aminoguanidine
D-P = reaction in presence of D-penicillamine
Mw = standard (daltons)
M and D - migration position of
histone H1 monomer and dimer C = control between H1 and ADP-ribose
AG = reaction in presence of aminoguanidine
D-P = reaction in presence of D-penicillamine
Mw = standard (daltons)
M and D - migration position of
histone H1 monomer and dimer

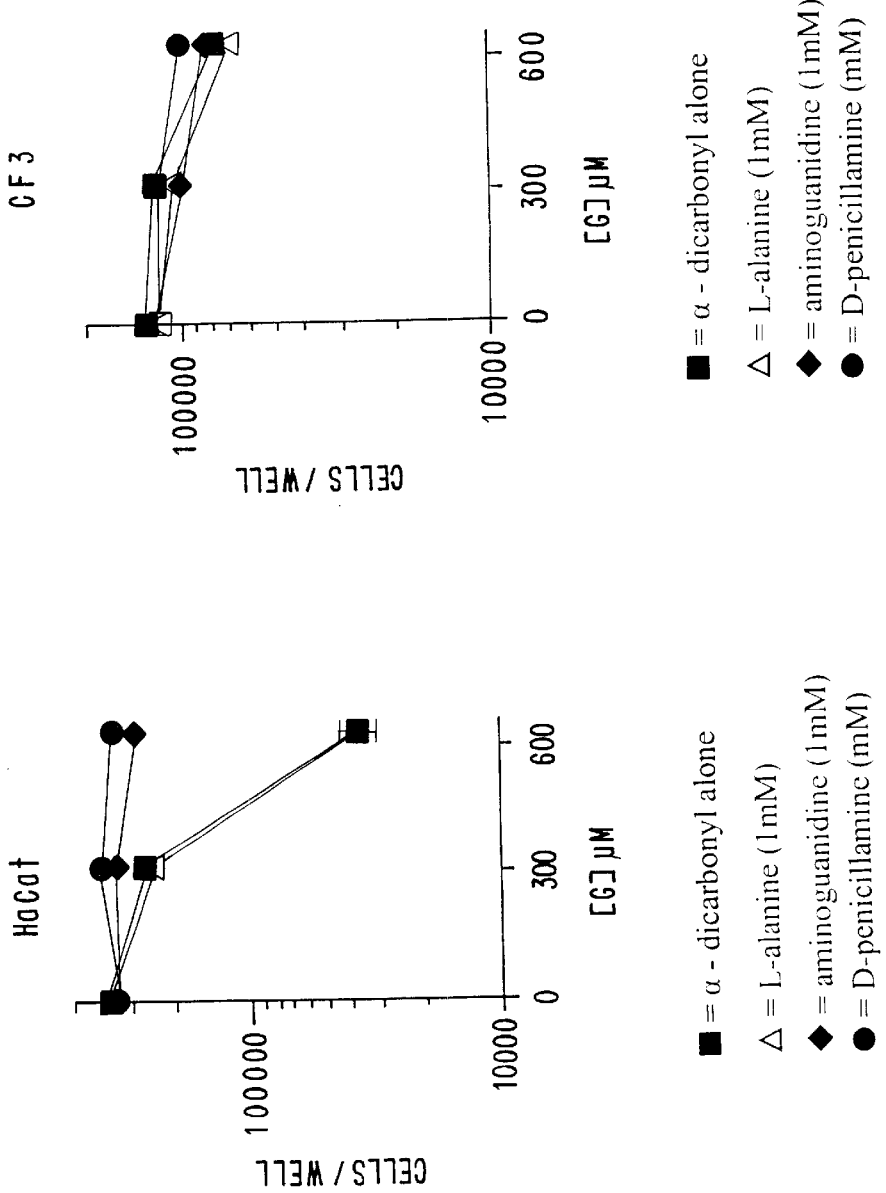

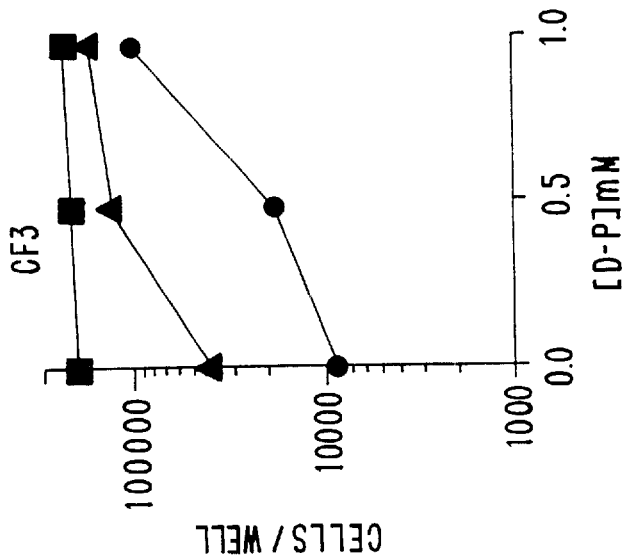
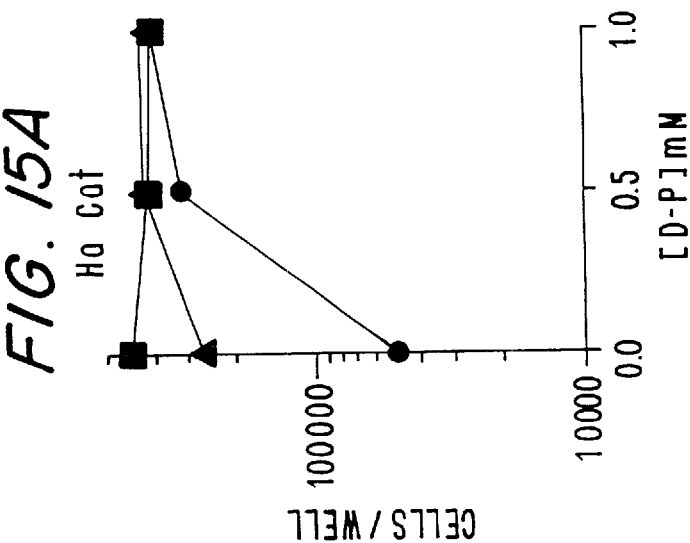

METHOD AND USE OF α-AMINO-β-MERCAPTO-ETHANE DERIVATIVES AS DICARBONYL SCAVENGERS FOR TREATMENT OF CONDITIONS RESULTING FROM PROTEIN, LIPID, AND DNA DAMAGE

This application claims priority from Provisional application Ser. No. 60/197,216, filed Apr. 14, 2000.

FIELD OF THE INVENTION

The present invention relates to a method of effectively preventing glycation-induced and other damage to proteins, lipids and DNA by scavenging dicarbonyl intermediates with penicillamine, penicillamine derivatives and other α-amino-β,β-mercapto-β,β-dimethyl-ethane derivatives as dicarbonyl trapping agents. The dicarbonyl scavenging activity of this class of compounds renders them useful as therapeutic agents for the prevention of and treatment of conditions associated with reactive carbonyl compounds and photodamage.

BACKGROUND AND SUMMARY OF THE INVENTION

Tissue deterioration and aging have long been associated with accumulation of chemical inducted protein and DNA damage. Reactive oxygen species (ROS) and reactive carbonyl species (RCS), especially α-dicarbonyl compounds, are key mediators of damage caused by oxidative stress, glycation, and UV-irradiation. Carbonyl stress additionally originates from the metabolic generation of methylglyoxal. The toxic effects of various mono- (e.g. 4-hydroynonenal) and α-dicarbonyls (e.g. glyoxal, methylglyoxal, deoxyosones) cannot be directly antagonized by antioxidants and only a small number of biological carbonyl scavengers like glutathione (GSH) have been identified.

The nonenzymatic reactivity of biomolecules is generally regarded as a major endogeneous source of damage to cells. Glycation is a nonenzymatic posttranslational modification of proteins by reducing sugars, which adversely affects protein function. These are subsequently converted to advanced glycosylation end products (AGEs) which represent a heterogenous class of reactive products which form spontaneously in vivo due to the reaction of glucose and other reducing sugars with amino groups of proteins in a concentration dependent manner. These undergo further rearrangements, dehydrations and cross-linking with other proteins to form the AGEs which play a role in long term complications of aging and diabetes.

Lipid peroxidation is another deleterious reaction that targets membrane associated lipids by oxidative mechanisms. Damage to proteins, lipids and nucleic acids by the formation and cellular accumulation of AGEs and peroxidation products has been implicated in a number of age-related diseases including long term diabetic complications (see Thorpe, S: R., and J. W. Baynes. 1996. Role of the Maillard reaction in diabetes mellitus and diseases of aging. *Drugs Aging.* 9:69–77), atherosclerosis (see Ruderman,N. B., J R. Williamson, and M. Brownlee. 1992. Glucose and diabetic vascular disease [published erratum appears in *FASEB J* 1993 Jan;7(1):237]. *FASEB J.* 6:2905–2914), Alzheimer's disease (see Vitek, M. P., K. Bhattacharya, J. M. Glendening, E. Stopa, H. Vlassara, R. Bucala, K. Manogue, and A. Cerami. 1994. Advanced glycation end products contribute to amyloidosis in Alzheimer disease. *Proc Natl Acad Sci U SA.* 91:4766–4770) chronic inflammation and the general pathology of the aging process (see Frye, E. B., T. P. Degenhardt, S. R. Thorpe, and J. W. Baynes. 1998. Role of the Maillard reaction in aging of tissue proteins. Advanced glycation end product-dependent increase in imidazolium cross-links in human lens proteins. *J. Biol Chem.* 273:18714–18719). Glycation and lipid peroxidation are characterized by the formation of very reactive, toxic dicarbonyl derivatives such as glyoxal, methylglyoxal, malondialdehyde, and 3-desoxyosones (Thomalley, P. J., Langborg, A., and Minhas, H. S. 1999. Formation of glyoxal, methylglyoxal and 3-deoxyglucosone in the glycation of proteins by glucose. Biochem. J. 344, 109–116). The crucial role of the generation of reactive carbonyl intermediates, especially dicarbonyl compounds, for the above-mentioned pathologies is well established and has led to the elaboration of the carbonyl hypothesis of aging (Yin, D. 1995. Studies on AGE pigments evolving into a new theory of aging. Gerontology 41, 159–172).

The arginine-derived imidazolium AGE-products (Lander, H M et al. Activation of the receptor for advanced glycation end products triggers a p21 (ras)-dependant mitogen-activated protein kinase pathway regulated by oxidant stress. J. Biol. Chem 272:17810–4, 1997), the glyoxal-lysine dimer (GOLD) and the methylglyoxal-lysine dimer (MOLD) (Brinkmann, Frye E et al., Role of Malliard reaction in aging tissue proteins, Advanced glycation end product-dependant increase in imidazolium cross-links in human lens proteins. J. Biol. Chem. 273:18714–18719, 1998) have been identified imaged human lens crystallin and skin collagen implicating alpha-dicarbonyl stress in tissue aging. Additionally, RCS like glyoxal, the direct precursor of the AGE $N^\epsilon$-carboxymethyl-L-lysine (CML), are generated by free radical damage to polyunsaturated fatty acids in cellular membranes (Fu, M. X. et al., The advanced glycation end product, Nepsilon-(carboxymethyl)lysine, is a product of both lipid peroxidation and glycoxidation reactions. J. Biol. Chem.271:9982–6,1996). UV-irradiation is another source of tissue carbonyl stress, as evidenced by the accumulation of CML in sun exposed lesions of actinic elastosis (Mizutari, K. et al., Photo- enhanced modification of human skin elastin in actinic elastosis by N(epsilon)-(carboxymethyl)lysine, one of the glycoxidation products of the Malliard reaction J. Invest. Dermatol. 108:797–802, 1997. Therefore, AGE-products like CML and GOLD may be regarded as biomarkers of tissue carbonyl stress.

Methylglyoxal is an important glycation intermediate (Thornally et al. Biochem J. 344:109–116, 1999), that is also generated as a biological metabolite by nonenzymatic and enzymatic degradation of glycolic triose phosphate intermediates and from threonine catabolism (Thornally, Pharmacology of Methylglyoxal: Formation, Modification of Proteins and Nucleic Acids and Enzymatic Detoxification-A role in Pathogenesis and Antiproliferative Chemotherapy, Gen. Pharmac. 27: 565–573, 1996). Increased levels of methylglyoxal are found in blood from diabetic patients Beisswenger et al. Metformin reduces systemic methylglyoxal levels in type 2 diabetes, Diabetes 48:198–202, 1999. and in the lens of streptozotocin-induced diabetic rats. A recent study on the formation of AGEs in endothelial cells cultured under hyperglycemic conditions indicated that methylglyoxal was the major precursor of AGEs (Shinohara, M. et al., Overexpression of glyoxalase I in bovine endothelial cells inhibits intracellular advanced glycation end-product formation and prevents hyperglycemia-induced increases in macromolecular endocytosis. J. Clin. Invest. 101:1142–7, 1998). Various methylglyoxal-derived AGEs have been identified in human tissues, such as fluorescent 5-methylimidazolone-derivatives in atherosclerotic lesions of the aorta (Uchida, K. et al. Protein modification by a Malliard reaction intermediate methylglyoxal. Immunochemical detection of fluorescent 5-methylimidazolone derivatives in vivo. FEBS Lett. 410:313–318,1997. or MOLD and $N^\epsilon$-carboxymethyl-L-lysine in aged skin collagen (Brinkmann supra) Recently, the cytotoxic effects of the glycation intermediates methylglyoxal and 3-deoxyglucosone on neuronal cells such as PC12 cells (Suzuki, K et al. Overexpression of aldehyde reductase protects PC12 cells from the cytotoxicity of methylglyoxal or 3-deoxyglucosone, J. Biochem (Tokyo) 123:353–7, 1998) and cultured cortical neurons Kikuchi, S. et al. Neurotoxicity of methylglyoxal and 3-deoxyglucosone on cultured cortical neurons: synergism between glycation and oxidative stress, possibly involved in neurodegenerative diseases. J. Neurosci. Res. 57:280–289, 1999. have attracted considerable attention because of their suspected participation in the pathogenesis of neurodegenerative diseases such as Alzheimer's disease (Vitek, M. P. et al., Advanced glycation end products contribute to amyloidosis in Alzheimer disease Proc. Natl. Acad. Sci. USA, 91:4766–70,1994) and amyotrophic lateral sclerosis Shinpo, K. et al. Selective vulnerability of spinal motor neurons to reactive dicarbonyl compounds, intermediate products of glycation, in vitro, implication of inefficient glutathione system in spinal motor neurons. Brain Res. 861:151–159, 2000.

As another result of oxidative and carbonyl stress, protein damage by carbonylation has been associated with aging and a number of diseases, such as the premature aging diseases, Progeria and Werner's syndrome (Berlett, B. S. et al., Protein oxidation in aging, disease and oxidative stress. J. Biol. Chem. 272:20313–20316, 1997). The amount of carbonyl groups in human skin fibroblast proteins strongly correlates with the age of the donor (Oliver, C, N, et al. Age-related changes in oxidized proteins. J. Biol. Chem. 262:5488–5491, 1987). Elevated levels of histone H1 carbonylation in vivo as an indicator of nuclear oxidative and glycoxidative stress have been reported Wondrak, G.T. et al. Histone carbonylation in vivo and in vitro, Biochem J. 351:769–777, 2000.

In contrast with their therapeutic potential, only a very limited number of biological inhibitors of cellular carbonyl stress like the nucleophilic carbonyl scavenger glutathione have been identified. However, some inhibitors of glycation interfere with the reaction by trapping intermediate alphacarbonyls, whereas other inhibitory substances act merely as antioxidants and transition metal chelators, thereby inhibiting advanced glycoxidation, but not glycation (Elgawish, A et al. Involvement of hydrogen peroxide in collagen crosslinking by high glucose in vitro and in vivo. J. Biol. Chem. 271:12964–71, 1996). Systemic administration of the hydrazine derivative and carbonyl reagent aminoguanidine, a member of the first class of glycation inhibitors, effectively suppresses secondary complications in diabetic rodents with experimental diabetes and inhibits skin collagen crosslinking (Edelstein, D. et al., Mechanistic studies of advanced glycosylation end product by aminoguanidine. Diabetes 41:26–9, 1992; Fu, M. X. et al., Glycation, glycoxidation, and cross-linking of collagen by glucose, Kinetics, mechanisms and inhibition of late stages of the Malliard reaction, Diabetes 43: 676–83, 1994). A nucleophilic bidentate, phenylacylthiazolium bromide, has been shown to protect *E. coli* against methylglyoxal toxicity Ferguson et al. Detoxification of methylglyoxal by the nucleophilic bidentate, phenylacylthiazolium bromide, Chem. Res. Tox. 12:617–622, 1999). Other nucleophilic compounds acting as carbonyl traps like tenilsetam (Shoda, H et al., Inhibitory effects of tenilsetam on the Malliard reaction. Endocrinology 138:1886–92,1997), pyridoxamine (Onorato, J. M. et al. J. Biol. Chem. 275:21177–21184, 2000) and metformin Ruggerio-Lopez et al. Reaction of metformin with dicarbonyl compounds. Possible implications in the inhibition of advanced glycation end product formation, Biochem. Pharm. 58:1765–1773, 1999) are being evaluated for prevention of secondary diabetic complications.

In vitro-screening for potential alpha-dicarbonyl scavengers is complicated by the nature of most of the currently employed glycoxidative reaction systems, which measure the suppression of oxygen dependent AGE-formation assessed by AGE fluorescence or immunological quantification of specific AGEs like CML. Consequently, in these glycoxidation systems AGE formation is effectively inhibited by compounds with antioxidant and metal chelating activity. Oxygen-independent advanced glycation by pentoses with formation of AGE fluorescence and protein crosslinking has been demonstrated and mechanistically linked to nonoxidative formation of deoxypentoses as reactive alpha-dicarbonyl intermediates Litchfield, J. E. et al. Oxygen is not required for the browning and crosslinking of protein by pentoses: relevance to Malliard reactions in vivo. Int. J. of Biochem. Cell Biol 31:1297–1305, 1999. Based on the identification of an accelerated glycation reaction between the phosphate-substituted pentose ADP-ribose and histone H1, which produces AGEs without involvement of oxygen Wondrak supra, the assay described herein was developed to screen glycation inhibitors acting as carbonyl scavengers.

It is an object of the present invention to prevent AGE formation and other types of damage caused by dicarboxyradicals, and to provide a protective effect to skin cells such as keratinocytes and fibroblasts from reactive carbonyl species.

The present invention provides a method for reducing protein, lipid, and DNA damage and change to skin cells by the administration of $\alpha$-amino-$\beta,\beta$-mercapto-$\beta,\beta$-dimethylethane derivatives, e.g., D-penicillamine, which react with dicarbonyls to prevent direct damage to important cellular macromolecules. Methods of inhibiting DNA and skin cell photodamage are also disclosed.

The present invention also relates to a screening method for the identification of carbonyl scavengers via a rapid glycation system that proceeds independent of oxygen and therefore excludes identification of inhibitory compounds acting as antioxidants.

BRIEF DESCRIPTION OF THE DRAWINGS

FIG. 9 is a flow diagram showing reaction of D-penicillamine with phenylglyoxal.

FIG. 12 shows aminoguanidine and D-penicillamine as inhibitors of non-oxidative advanced glycation of histone H1 by ADP-ribose.

FIG. 15 shows the protection of HaCat keratinocytes and CF3 fibroblasts from methylglyoxal induced alpha-dicarbonyl stress by D-penicillamine.

DETAILED DESCRIPTION

Figure 1:
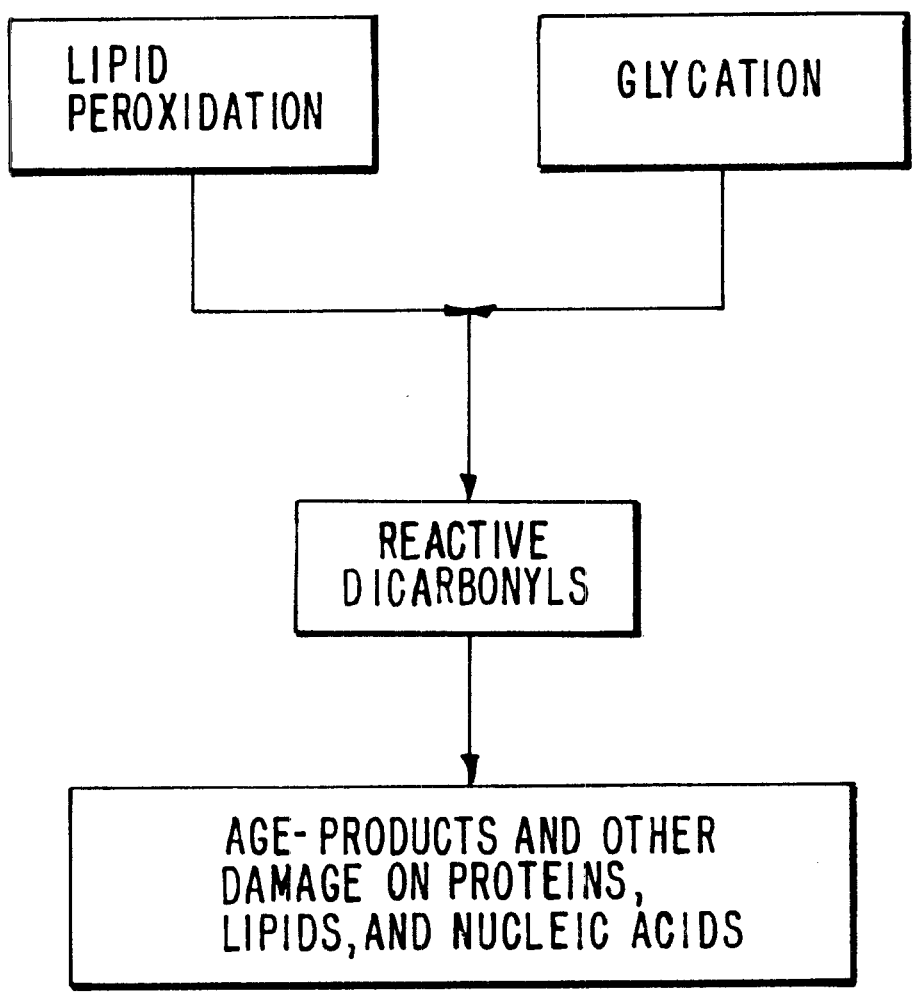
FIG. 1 is a flow diagram showing the formation of AGE-products resulting from glycated proteins.
Figure 2:
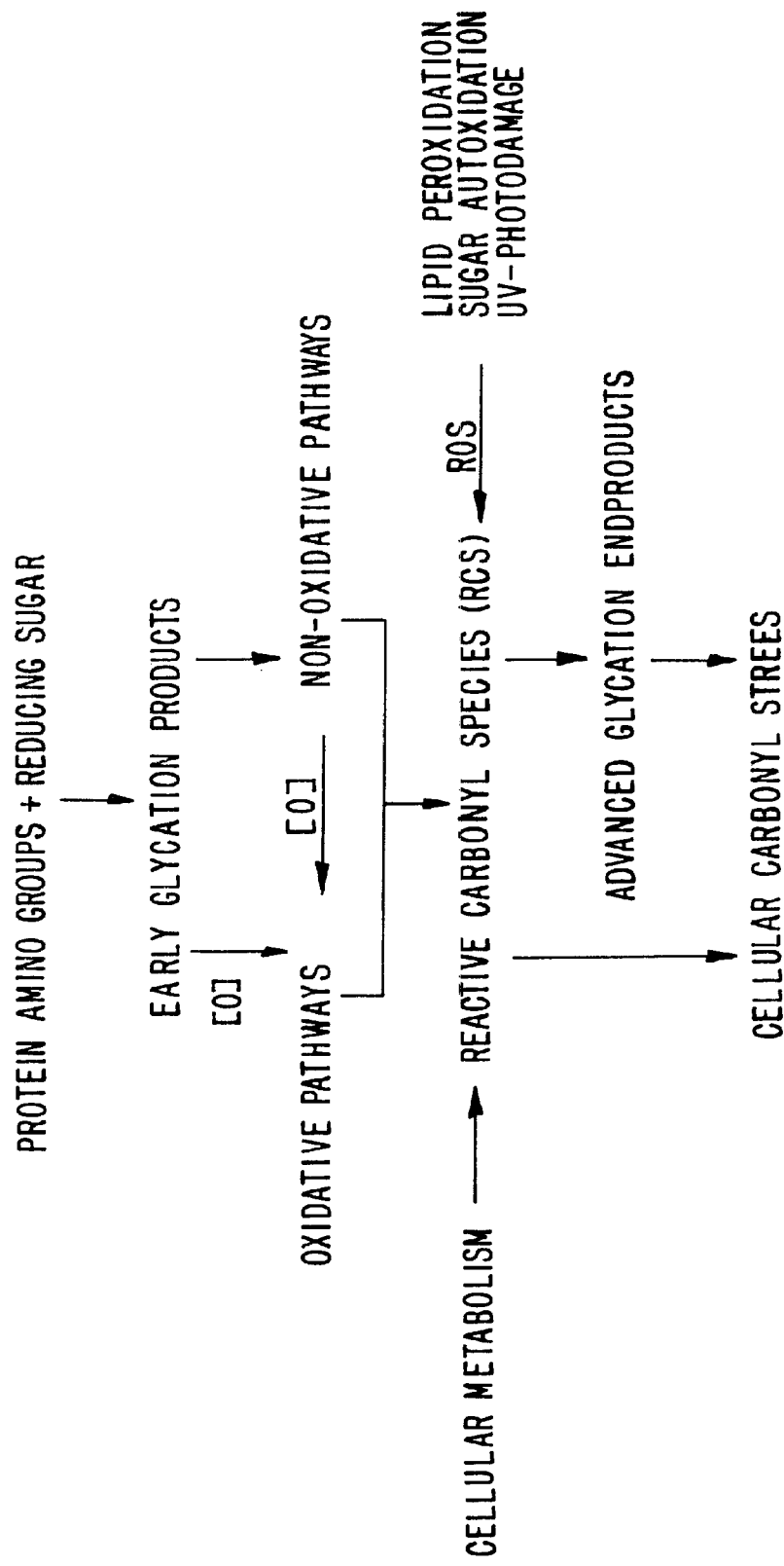
FIG. 2 is a more detailed flow diagram of the process shown in FIG. 1.

FIG. 1 is a flow diagram of protein glycation and lipid peroxidation and shows the involvement of reactive dicarbonyls that lead to accumulation of AGE-products and other damage on proteins, nucleic acids and lipids. FIG. 2 shows the process in more detail. Protein-AGE include protein $N^\epsilon$-(carboxymethyl)lysine residues (CML) (Ahmed, M. U., S. R. Thorpe, and J. W. Baynes. 1986. Identification of N epsilon-carboxymethyllysine as a degradation product of fructoselysine in glycated protein. *J. Biol Chem.* 261:4889–4894) and a heterogeneous group of complex modifications such as pentosidine (Sell, D R., and V. M. Monnier. 1989. Structure elucidation of a senescence crosslink from human extracellular matrix. Implication of pentoses in the aging process. *J. Biol Chem.* 264:21597–21602) that are characterized by their high fluorescence and ability to cause protein-protein cross-links. Accumulation of AGE-specific fluorescence (ex. 370 rim; em. 440 nm) is a general measure of overall protein damage and it is a widely used tool of glycation research in vitro and in vivo. In some cases, reactive dicarbonyl compounds may form by auto-oxidation of the sugar itself without requiring glycation, and the presence of trace amounts of transition metal ions (Fe, Cu) has been implicated in the formation of dicarbonyl compounds and reactive oxygen species such as hydrogen peroxide as reported by Elgawish, A., M. Glomb, M. Friedlander, and V. M. Monnier. 1996. Involvement of hydrogen peroxide in collagen cross-linking by high glucose in vitro and in vivo. *J. Biol Chem.* 271:12964–12971.

Research has demonstrated that the cell nucleus is a likely site for protein glycation in vivo by ADP-ribose (see Cervantes-Laurean, D., D. E. Minter, E. L. Jacobson, and M. K. Jacobson. 1993. Protein glycation by ADP-ribose: studies of model conjugates. *Biochemistry.* 32:1528–1534. Jacobson, E. L., D. Cervantes-Laurean, and M. K. Jacobson. 1994. Glycation of proteins by ADP-ribose. *Mol Cell Biochem.* 138:207–212. Cervantes-Laurean, D., E. L. Jacobson, and M. K. Jacobson. 1996. Glycation and glycoxidation of histones by ADP-ribose. *J. Biol Chem.* 271:10461–10469; Jacobson, E. L., Cervantes-LAureari, D., & Jacobson, M. K. 1997. ADP-Ribose in Glycation and Glycoxidation Reactions. Jn ADP-Ribosylation in Animal Tissues. H. Koch-Nolte, editor. Plenum Press, New York. 371–379; and Jacobson, E. L., D. Cervantes-Laurean, and M. K. Jacobson. 1997. ADP-ribose in glycation and glycoxidation reactions. *Adv Exp Med Biol.* 419:371–379).

Figure 3:
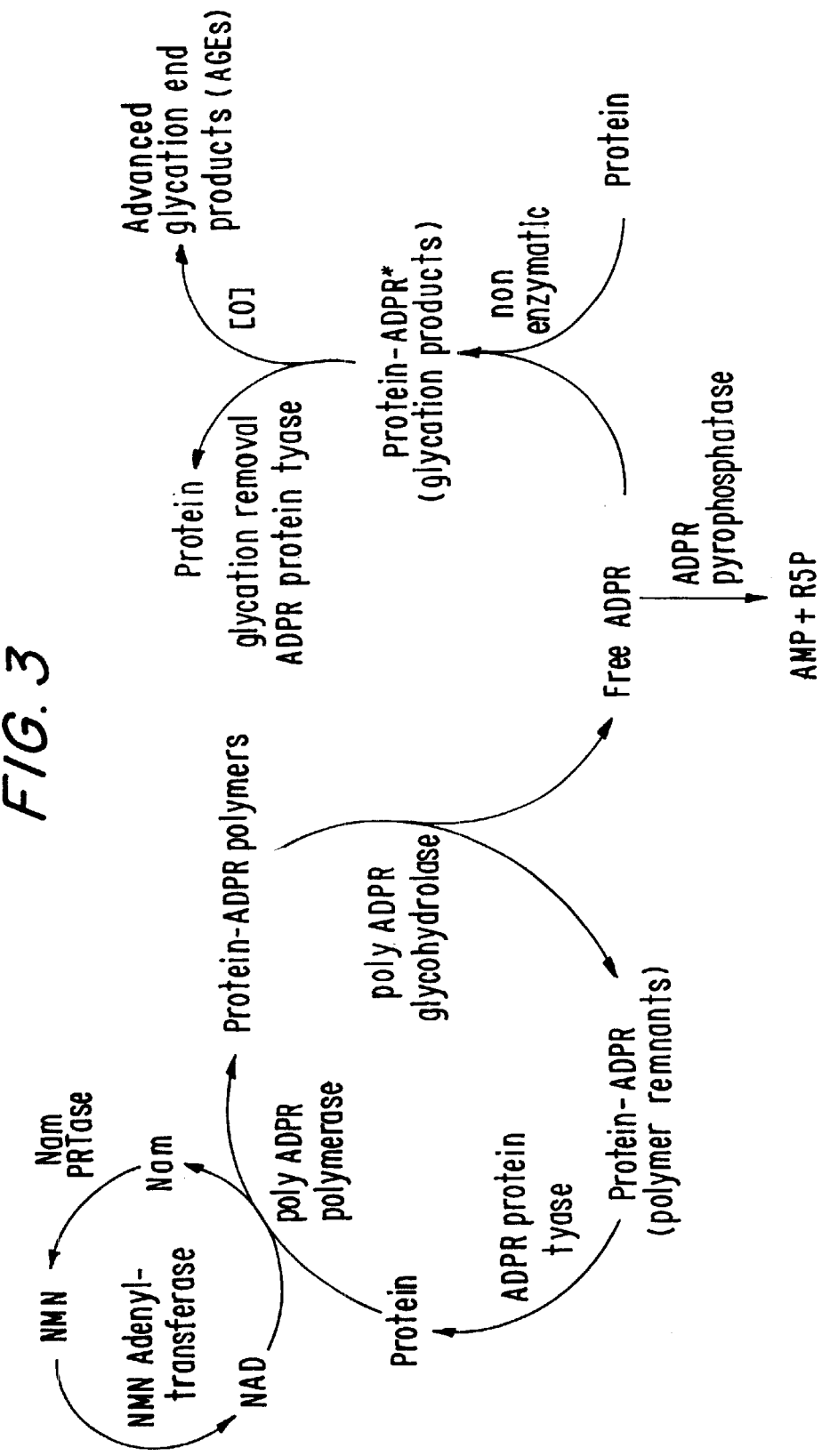
FIG. 3 is a proposed pathway showing the nonenzymatic formation of AGEs from proteins glycated with ADP ribose as an example of protein damage.
Figure 4:
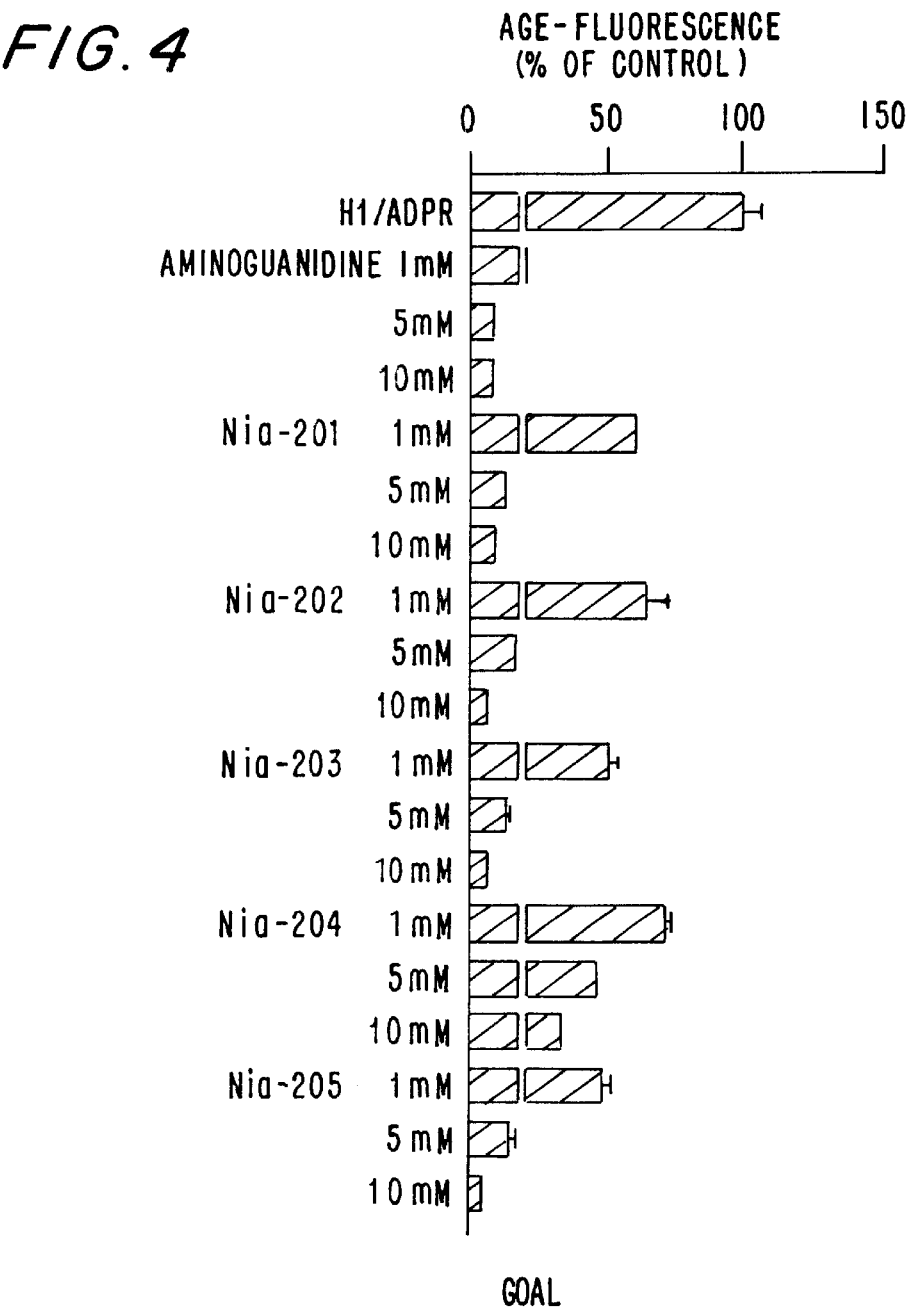
FIG. 4 is a graph showing AGE-fluorescence of H1-ADPR (standard), and reduction of AGE-fluorescent with aminoguanidine and various penicillamines.
Figure 5:
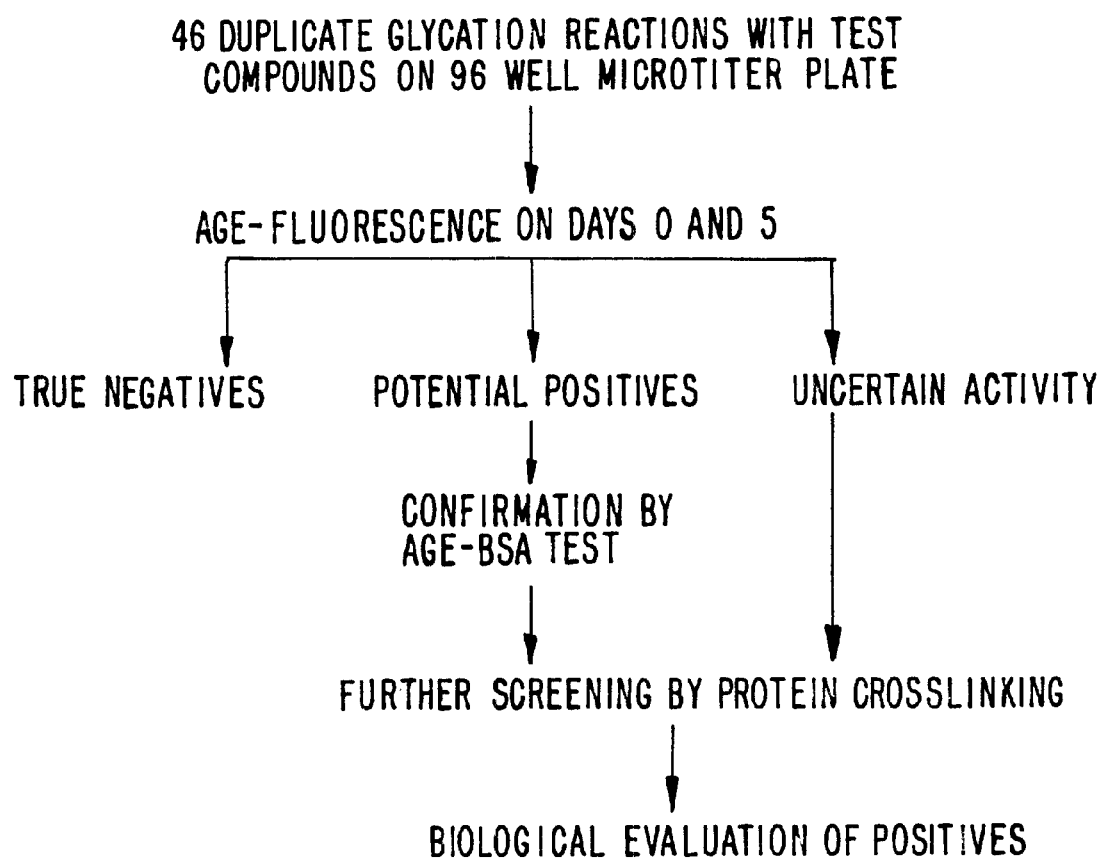
FIG. 5 is a schematic of the plate screening mechanism of the invention.

Oxidative stress and other conditions that cause DNA strands breaks stimulate the synthesis of nuclear polymers of ADP-ribose, which are rapidly turned over generating ADP-ribose in close proximity to the long lived histones rich in lysine and arginine residues as depicted in FIG. 3. Based on this research a simple reaction system was established allowing the assessment of nuclear glycation damage and its supression by inhibitory substances.

As mentioned above, glycation and subsequent protein-AGE formation plays a central role in glucose toxicity. Administering the glycation inhibitor aminoguanidine effectively suppresses secondary complications in rodents with experimental diabetes (Edelstein, D., and M. Brownlee. 1992. Aminoguanidine ameliorates albuminuria in diabetic hypertensive rats. *Diabetologia.* 35:96–97). Aminoguanidine is thought to act as a dicarbonyl scavenger, therefore inactivating toxic reactive dicarbonyl compounds. However, aminoguanidine is a hydrazine derivative that shows systemic toxicity upon long-term administration, since it is a potent inhibitor of catalase (Ou, P., and S. P. Wolff. 1993. Aminoguanidine: a drug proposed for prophylaxis in diabetes inhibits catalase and generates hydrogen peroxide in vitro. *Biochem Pharmacol.* 46:1139–1144) and inducible nitric oxide synthase (Okuda, Y., S. Sakoda, H. Fujimura, and T. Yanagihara. 1998. Aminoguanidine, a selective inhibitor of the inducible nitric oxide synthase, has different effects on experimental allergic encephalomyelitis in the induction and progression phase. *J Neuroimmunol.* 81:201–210). The toxicity profile of aminoguanidine makes it a poor candidate for clinical use. Therefore, a need exists in the medical art for new compounds that effectively inhibit glycation and its associated pathological consequences. The following examples demonstrate the trapping reaction of the alpha-oxoaldehydes methylglyoxal and phenylglyoxal by a-amino-α,β-mercapto-β,β-dimethyl-ethane derivatives such as penicillamine for protection of human skin against carbonyl stress.

DETAILED DESCRIPTION OF PREFERRED EMBODIMENTS

EXAMPLE 1

Chemicals

All chemicals were from Sigma Chemical co. Calf tissue (thymus) frozen in liquid nitrogen immediately after collection, was from Pel-Frez Biologicals.

Preparation of Glycosylated Bovine Serum Albumin (AGE-BSA)

AGE-BSA was prepared as described by Takata K H, Araki N, Shiga M, Saitoh M, Morino Y, Endocytic uptake of nonenzymatically glycosylated proteins is mediated by a scavenger receptor for aldehyde-modified proteins. *Biochemistry* 263: 14819–25, 1988. Briefly, 1.6 g of BSA and 3.0 g of D-glucose were dissolved in 10 mL of 0.5 M sodium phosphate buffer, pH 7.4, containing 0.05% $NaN_3$. The solution was filter sterilized through a 0.45 μm filter and incubated in the dark for 90 days at 37° C. Following dialysis against water, the sample was lyophilized.

Isolation of Histone H1 from Calf Thymus

All operations were carried out at 4° C. Chromatin was isolated from fresh calf thymus by extraction with 0.14 M NaCl, 0.05 M $Na_2S_2O_5$, as described earlier in Wondrak supra. After repeated extraction with 5% $HCl)_4$ and centrifugation (1500 g), histone H1 was precipitated from the supernatant by addition of TCA (20% final concentration v/v). The histone H1 precipitate was colleted by centrifugation (12,000 g) and deionized water. After extensive dialysis (MW cut-off: 12,000–14,000) against water for 48 h, the sample was lyophilized and the protein was stored at 4° C. SDS-PAGE (12%) was used to analyze the purity of the preparation.

Glycation of histone Hl by ADP-ribose is fully inhibited bypenicillamine and penicillamine derivatives. Earlier studies have reported that D-penicillamine inhibits collagen crosslinking and AGE fluorescence caused by sugars (McPherson, J. D., Shilton, B. H., and Walton, D. J. 1988. Role of Fructose in Glycation and Cross-Linking of Proteins. Biochemistry 27, 1901–1907) and reaction of D-penicillamine with aldehyde groups of proteins (Deshmukh, K., and Nimm, M. E. 1969. A Defect in the Intramolecular and Intermolecular Cross-linking of Collagen caused by Penicillamine. J. Biol. Chem. 244, 1787–1795). A number of different penicillamines and penicillamine derivatives were tested to determine the inhibition of AGE-fluorescence on histone H1 at physiological pH. The reaction conditions for the glycation of histone H1 by ADP-ribose mimic physiological conditions to the extent possible. Reaction mixtures contain 1.5 mg/ml histone Hl, 1.0 mM ADP-ribose, 50 mM potassium phosphate buffer, pH 7.4, 37° C. D,L-penicillamine; L-penicillamine; D-penicllamine; D-penicillaminedisulfide and N,S-isopropylidine-D-penicillamine were tested in concentrations of 1,5 and 10 mM. The detected reaction parameter representing the accumulation of protein damage is AGE-fluorescence (($\lambda$ex=370 nm; $\lambda$em= 440 nm), which is suppressed by the presence of a compound with inhibitory activity. Generation of AGE-type fluorescence ($\lambda$ex=355 nm; $\lambda$em=405 nm) was monitored over time at 37° C; which is in the range of the broad excitation/emission maxima of AGE compounds. To allow high throughput sample processing on 96 well microtiter plates, the reaction volumes are 300 $\mu$l. Fluorescence on the 96-well microtiter plates was measured using an automated microtiter fluorescence reader. Fluorescence of the 1 ml samples of the glycation reaction mixtures was measured using a Hitachi F-200 fluorescence spectophotometer, and prior to measurement the protein sample is dialyzed extensively against water (MW cutoff= 10,00 Daltons), lyophilized and reconstituted in reaction buffer. For inhibitor screening the plate is read on a Fluoroskan II plate reader (Titertek, ICN) at the excitation/ emission wavelengths set forth above at a bandwidth of 35 nm.

The following screening scheme is used (see Table 1): AGE-fluorescence is determined at the beginning and after five days of incubation. Test compounds that are inherently fluorescent (designated false negatives) were identified by the initial fluorescence measurement (See Table 1, NADH for example). Since these are compounds of uncertain activity, they are diverted directly to the second stage of the screen. Aminoguanidine, a known glycation inhibitory agent, was used as a positive control for suppression of the increase on AGE-fluorescence. After five days incubation and plate reading, fluorescence quenchers (designated false positives) are excluded by measuring the quenching activity of the test compound by addition of AGE modified protein having known fluorescence activity to one microtiter plate well containing test compound in the complete reaction mixture. For this, AGE-BSA is used as the AGE-type fluorescence standard. This AGE-BSA test excludes false positives compounds that function by fluorescence quenching. If fluorescence quenching occurs the test compound is excluded from further screening. Potential positive compounds are further analyzed by measuring inhibition of protein-crosslinking by 12% SDS-PAGE analysis of a 3 microliter aliquot taken from the reaction well on the plate. The protein is visualized by silver staining of the gel. Untreated histone H1 and the positive control containing aminoguanidine are loaded onto the gel together with the samples of potential positive test compounds. A compound that passes the first and second stage of the screen is considered a glycation inhibitor and is further evaluated for biological activity as described below.

Figure 6A:
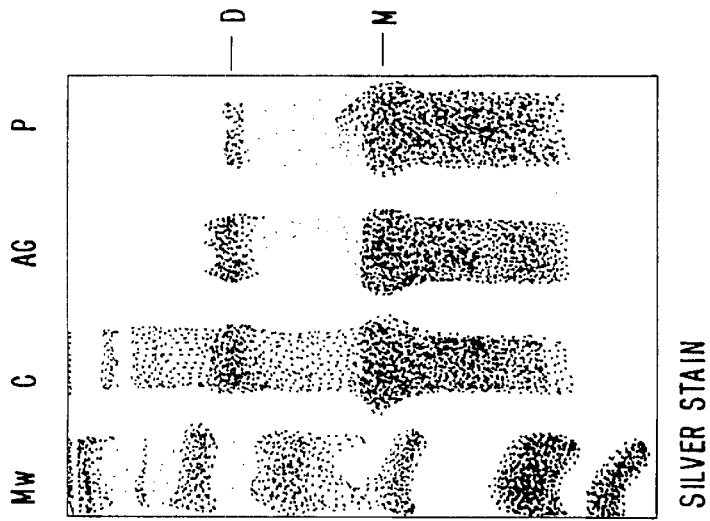
FIG. 6 are SDS-PAGE assays of H1/ADPR crosslinking and inhibition by D-penicillamine and aminoguanidine.
Figure 6B:
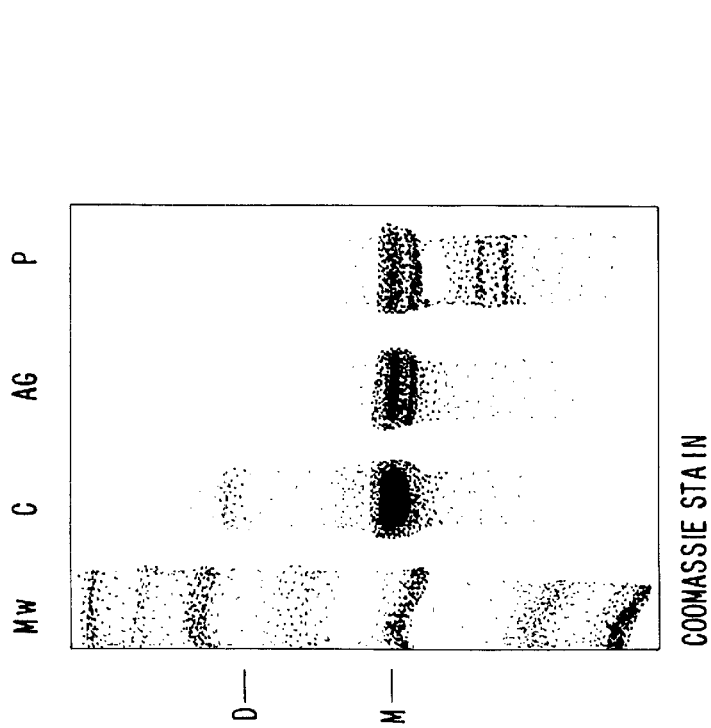

D-penicillamine (5 mM) and aminoguanidine (5 mM) were shown to inhibit histone H1 crosslinking measured by 12%-SDS-PAGE followed by silver staining as described (FIG. 6). Crosslinking was detected with high sensitivity in a histone H1, ADP-ribose reaction system paralleling formation of high AGE-type fluorescence (C), inhibition with aminoguanidine (AG), inhibition with D-penicillamine (P).

Preparation and Structure Elucidation of the D-penicillamine-Methylglyoxal Reaction product as 2-acetyl-5,5-dimethyl-thiazolidine-4-carboxylic acid To a solution of D-Penicillamine (350 mg, 2.3 mmol) in 50 ml of aqueous 0.20 M phosphate buffer (pH7.4) was added MG (40% in water/620microiliters, 3.45 mmol). Te reaction mixture was stirred at 37° C. for 24 h. The solvent was concentrated to half volume at reduced pressure and the residue was desalted on Amberchrome CG 71 ms resin (1.5×45 cm) (TosoHaas, Philadelphia, Pa.). The column was developed with water. The UV absorbing peaks were pooled, and the water was evaporated at reduced pressure, The crude product was purified by anion exchange chromatography on a 1.5×45 column of QAE Sephadex 25 (Sigma), developed by application of a linear gradient formed between 200 ml of distilled water and 200 ml of 0.2M NH4HCO3. Fractions were collected, and absorbance at 254 nm was measured. Fractions constituting a single major peak eluting about midway in the gradient were pooled and concentrated. The 1H-NMR spectrum exhibited the following signals: ($\delta_H$ D2O in ppm): 1.03 (3H,s,CH3), 1.90 (3H,s,CO—CH3), 3.96 and 3.98 (diastereomeric, 1H,s,CH—COOH). Mass spectrometric analysis by MALD-TOF-MS revealed a (M+Na)$^+$ of 226 Daltons.

Figure 7:
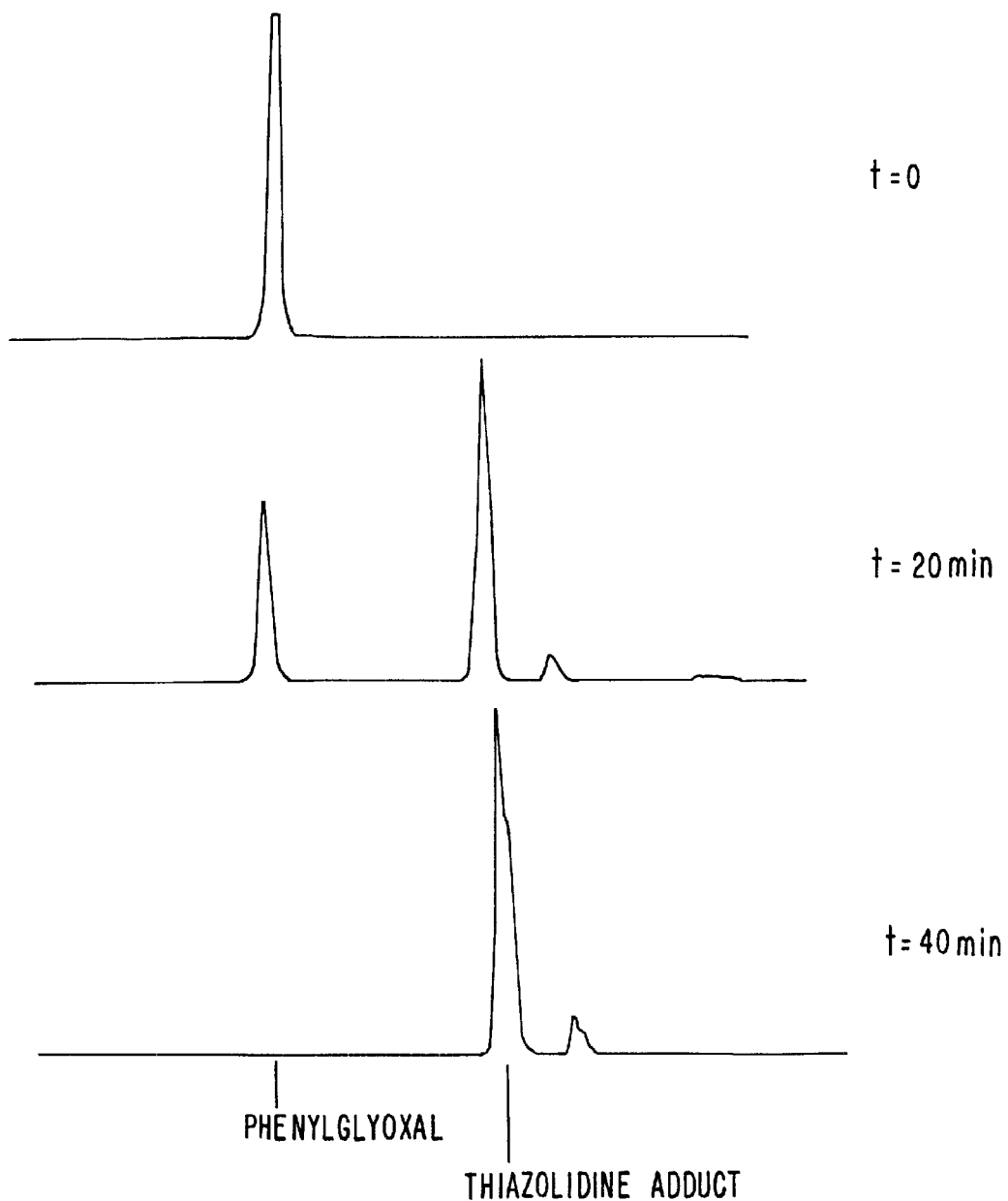
FIG. 7 are the reverse phase HPLC results showing the scavenging activity of D-penicillamine on the dicarboxyl phenylglyoxal.

Preparation and Structure Elucidation of the D-Penicillamine-Phenylglyoxal reaction product as 2-benzoyl-5,5-dimethyl-thiazolidine-4-carboxylic acid Phenylglyoxal (10 mM) and D-penicillamine (20 mM) were reacted in 50 mM KH2PO4 buffer, pH 7.4 at room temperature. The progress of he reaction was monitored by HPLC analysis of reaction aliquots at 254 nm. After 40 minutes reaction time more than 90% conversion of the phenylglyoxal peak into a single product peak of higher retention time was observed. The reaction product was obtained by preparative HPLC, lyophilized and analyzed by 1H-NMR spectroscopy. The spectrum exhibited the following signals: ($\delta_H$ D2O in ppm): 1.38 (3H,s,CH3), 1.45 (3H,s,CH3), 4.12 (1H,s,CH—COOH), 7.42–7.82 (5H,m, ArH). UV detection was at 254 nm. As shown by the HPLC analysis of the reaction system shown in FIG. 7, phenyglyoxal is fully reacted with D-penicillamine within 5 minutes.

Figure 8:
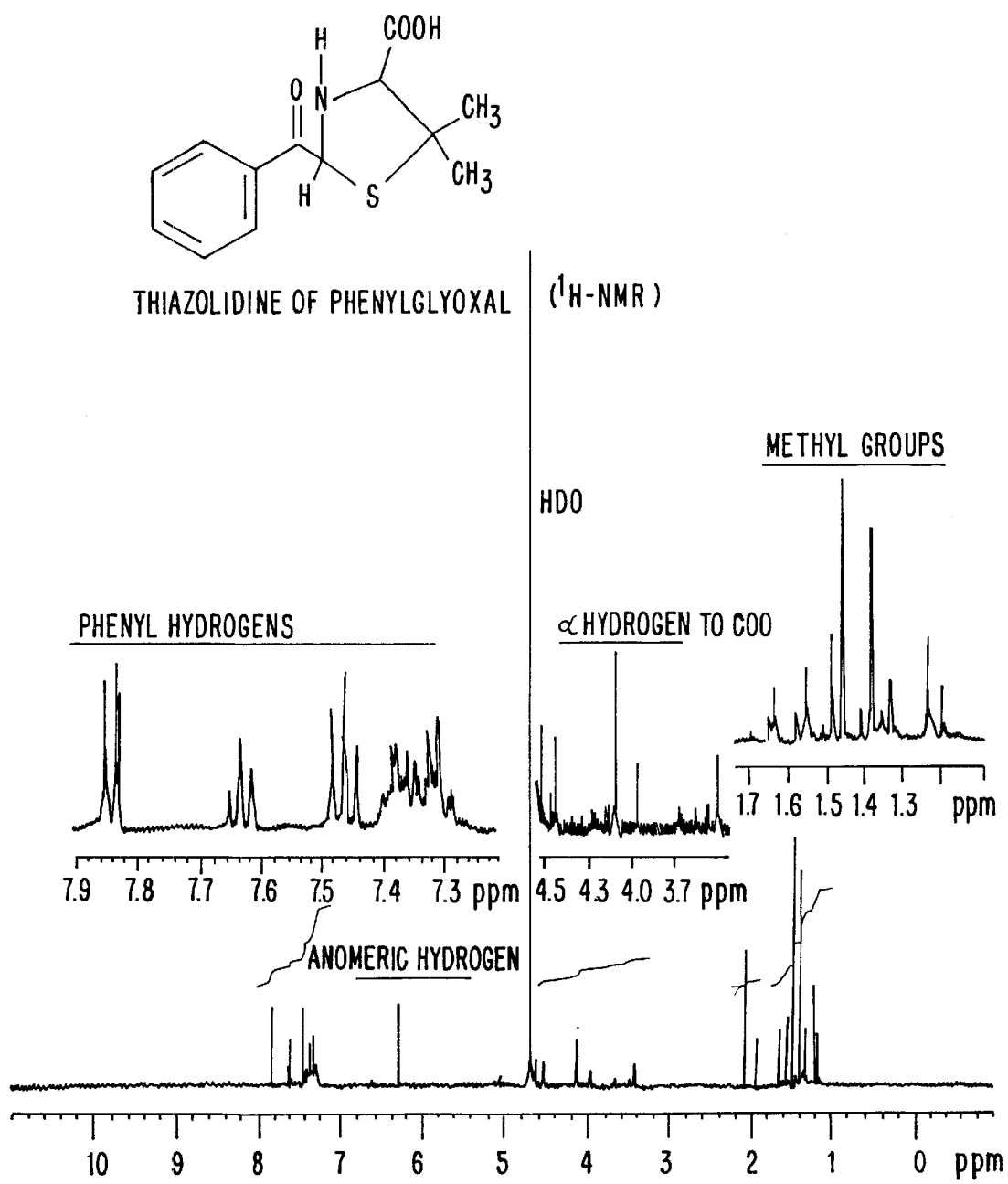
FIG. 8 is $^1$H- NMR spectrum of the thiazodine derivative of phenylglyoxal.

The $^1$H-NMR spectrum of the reaction product formed in the reaction is shown in FIG. 8. The product formed is a thiazolidine derivative whose proposed structure and the proposed mechanism of trapping is also shown in FIG. 8.

Penicillamines are effective dicarbonyl scavengers and may be administered to subjects to prevent AGE formation and other types of direct damage that result from dicarbonyls in vivo. Penicillamines will be administered to the subject in sufficient doses to accomplish these therapeutic goals, and will find particular use in the treatment of diabetics.

Reaction Kinetics of Alpha-dicarbonyl Trapping

The reaction of phenylglyoxal with test compounds were carried out in 10 mM phosphate buffer, pH 7.4 at 37° C. and were followed by HPLC analysis. The reaction kinetics were studied at a phenylglyoxal concentration of 50 micromoles and at 250 and 500 micromolar carbonyl scavenger concentration (D-penicillamine, aminoguanidine). Over the course of the reaction, aliquots were analyzed by HPLC. In the case of D-penicillamine, which required shorter sampling periods, reaction aliquots were taken every 20 seconds, and kept on dry ice until analysis. The initial reaction rates of phenylglyoxal with the test compounds were monitored by following the disappearance of phenylglyoxal over time. The reaction between phenylglyoxal and the test compounds is a second order reaction with a rate equation of $-dc/dt=K_{2nd}$ {phenylglyoxal} {dicarbonyl scavenger}. The reaction was conducted in the presence of excess test compounds (ratio of 1:5 and 1:10 phenylglyoxal to test compound), to convert it to pseudo-first order reaction kinetics as demonstrated by the apparent dependency of the reaction rate constant ($k_{1st}$) on the concentration of the test compound. A plot of Log AUC for phenylglyoxal versus time resulted in a slope equal to $k_{1st}/2.303$. The measured first order rate constant ($k_{st}$) was then used to calculate the second order rate constant (by applying the following equation: $k_{2nd}=k_{1st}$ {alpha-carbonyl scavenger}. The calculated second order rate constants determined at the two reactant ratios were in good agreement.

Cell Culture

A continuous cell line of human epidermal keratinocytes (HaCat cells) and human dermal fibroblasts (CF-3 cells) were routinely cultured in 75 cm² flasks and split biweekly in DMEM containing 10% fetal bovine serum and kept in a humidified atmosphere containing 5% $CO_2$ at 37° C. Human keratinocytes were split using 5% trypsin and human fibroblasts employed 1% trypsin. All experiments were carried out on 6 well dishes (Falcon USA), where keratinocytes were seeded at $2\times10^4$ cells/well and fibroblasts at $4\times10^4$ cells/well. Cells were left overnight to attach to the plate and the appropriate carbonyl scavenger was then added 15 minutes prior to the addition of the alpha-dicarbonyl stress compounds glyoxal or methylglyoxal. Following 72 hour exposure to the stress compound, cells were counted with a Coulter counter. the protective effects of the alpha-dicarbonyl scavengers were assessed by comparing the growth of untreated cells with cells exposed to alpha-carbonyl stress +/− test compound.

EXAMPLE 3

Figure 10:
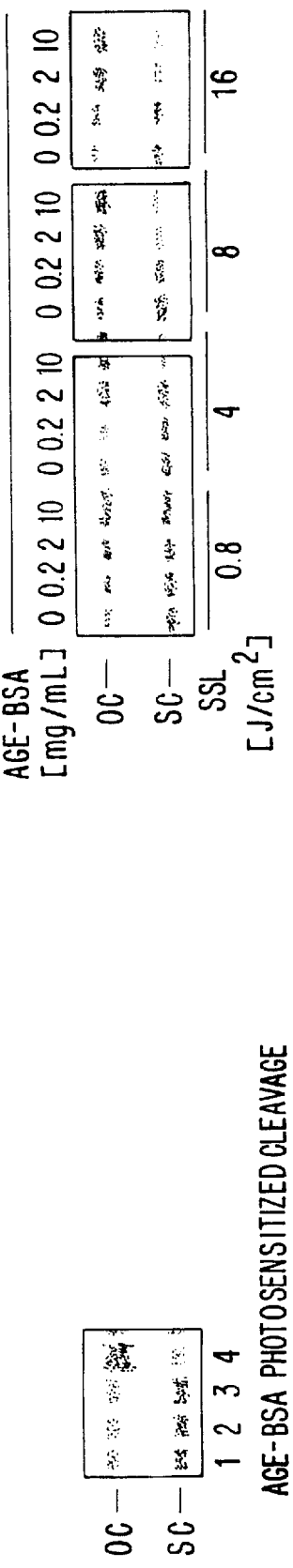
FIG. 10 show results of AGE-BSA photosensitized cleavage of ΦX-174 DNA from Example 3.
Figure 11:
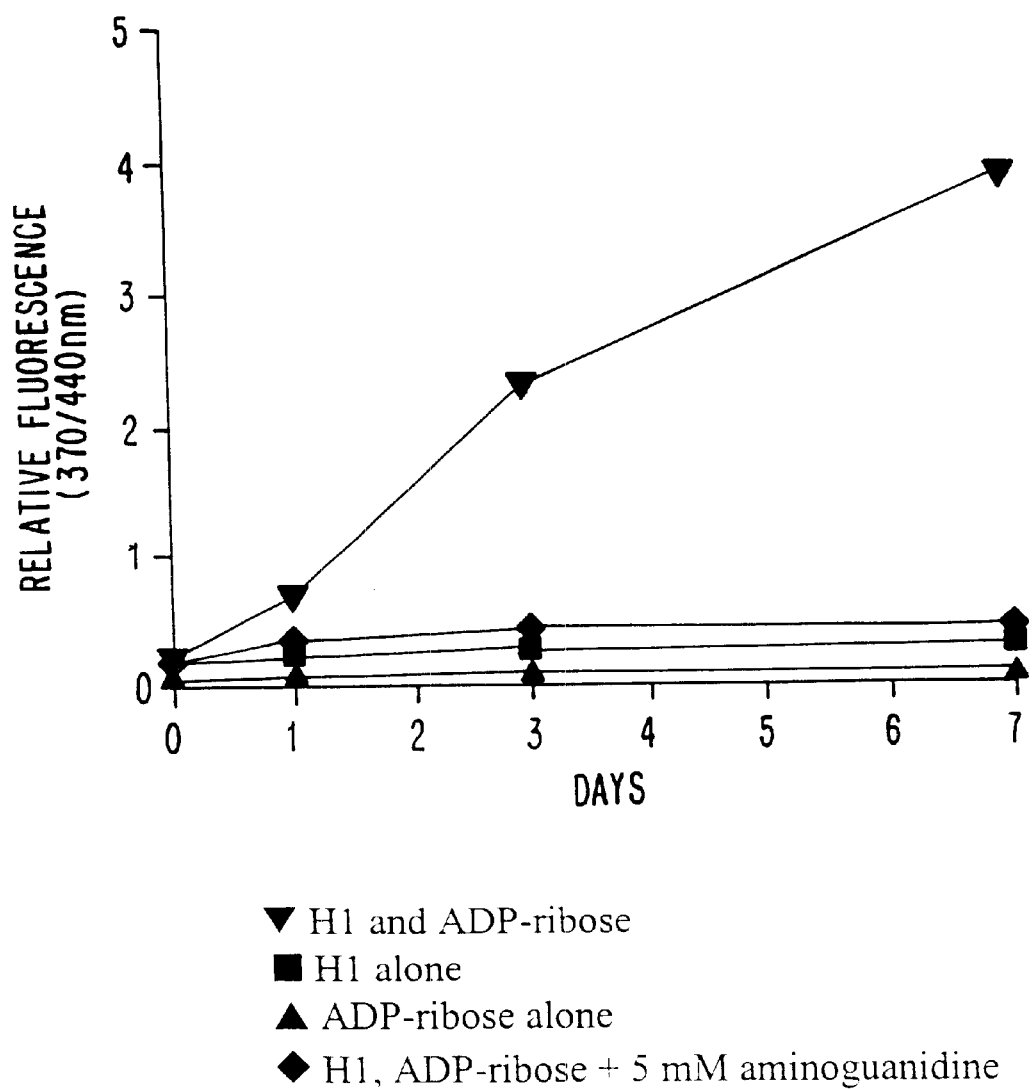
FIG. 11 is a graph of fluorescence v.s days showing the formation of AGE-fluorescence at pH 7.4.
Figure 13A:
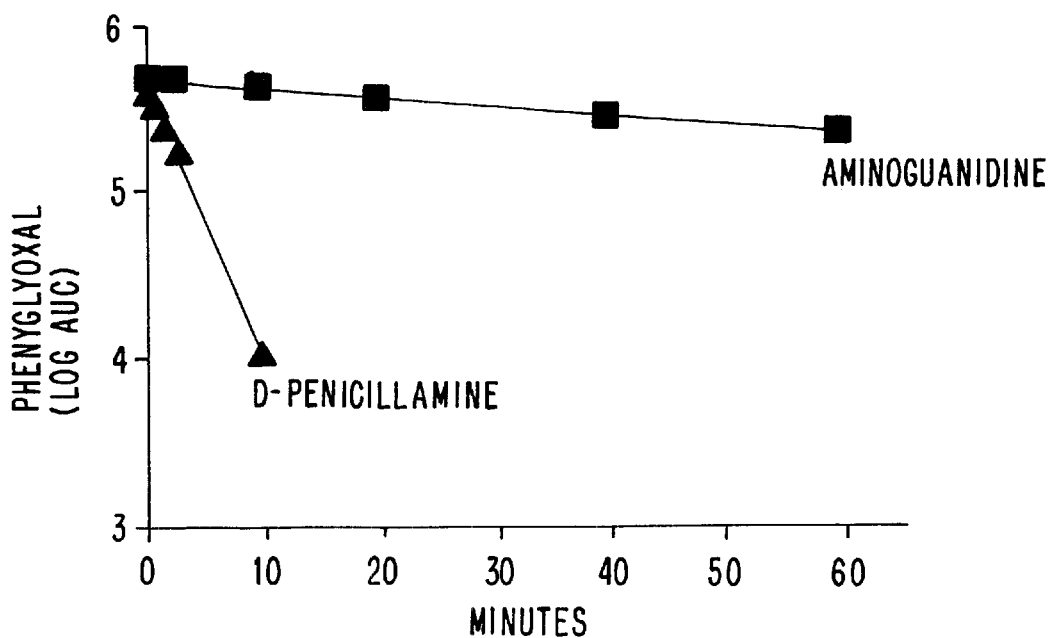
FIG. 13 are the comparative reaction kinetics of alpha-oxoaldehyde scavenging by D-penicillamine and aminoguanidine.
Figure 13B:
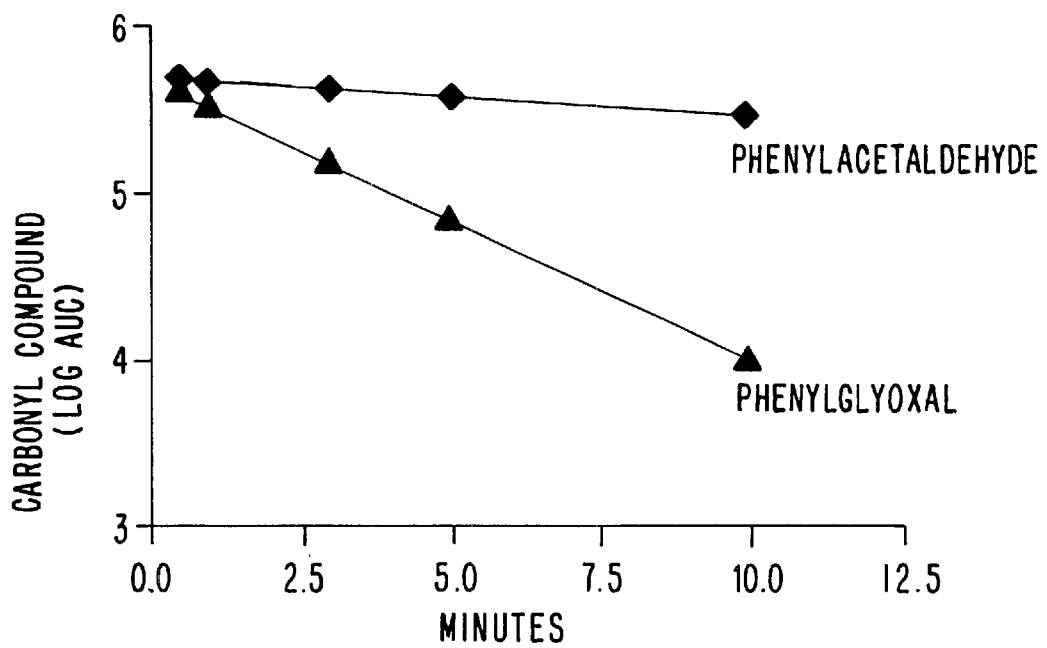
Figure 14A:
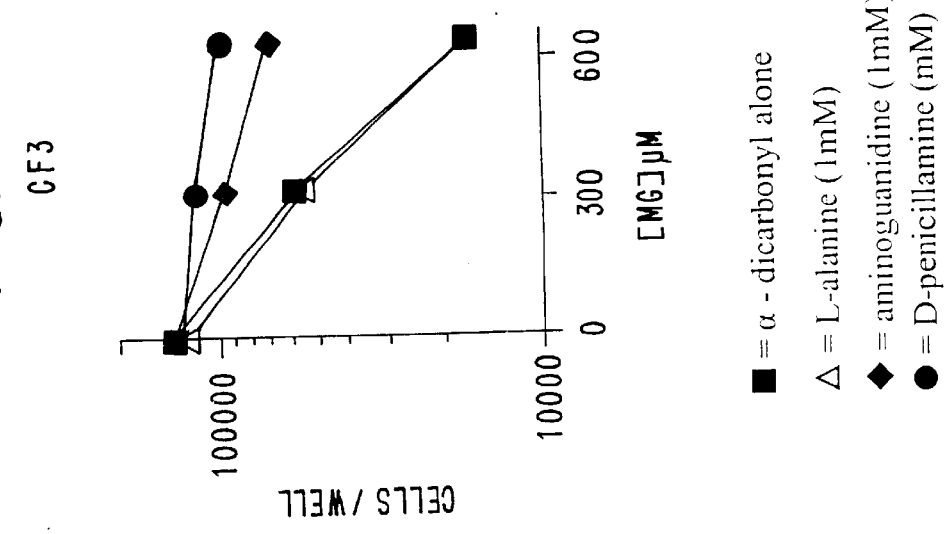
FIG. 14 shows the protection of HaCat human keratinocytes and CF3 fibroblasts from alpha-dicarbonyl stress in the presence of aminoguanidine and D-penicillamine.
Figure 14B:
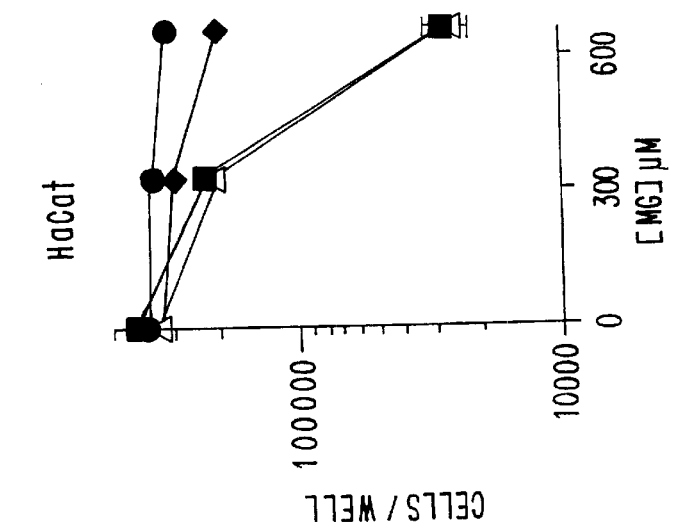

Glycated Proteins as Photosensitizers of DNA Damage in Skin Photoaging. D-Penicillamine inhibits genotoxic consequences of AGE-photosensitization. Accumulation of AGEs on dermal elastin and collagen occurs during normal skin aging in humans. The hypothesis was tested that the intra- and extracellular accumulation of the complex yellow-brown AGE-chromophores contributes to skin aging and carcinogenesis induced by chronic exposure to sunlight. As a possible molecular mechanisms for a detrimental synergism of AGE-formation and exposure to sunlight, photosensitized DNA damage by AGEs was assessed in a simple in vitro system. Irradiation of covalently closed circular ΦX-174 DNA with increasing doses of solar simulated light (SSL) in the presence of AGE-BSA was used to detect photosensitized DNA nicking as a measure of DNA photodamage (panel A). Upon exposure to SSL (0.8–16 J/cm²), the damage was concentration dependent with respect to AGE-BSA as the photosensitizer (panel B). Unmodified BSA displayed no such photosensitizing activity. Addition of several antioxidants modulated the photosensitization effect (panel C). Mannitol (a hydroxyl radical quencher) and $NaN_3$ (a singlet oxygen quencher) blocked the photosensitized DNA cleavage, whereas catalase and SOD were not effective, indicating the involvement of photoactivated oxygen and hydroxyl radicals. The thiol-antioxidant and RCS-scavenger D-penicillamine inhibited the photosensitization effect of AGE-BSA in a dose dependent relationship (panel D). Results are shown in FIG. 10.

Photosensitized DNA damage in skin is thought to be an important mechanism of UVA phototoxicity. Taken together with a recently published report on reduced viability of human dermal fibroblasts exposed to UVA irradiation in the presence of protein modified by AGEs, these preliminary results suggest that glycated skin proteins can function as photosensitizers of DNA damage. Future research efforts should clarify the genotoxic consequences of skin glycation implicated in this in vitro study.

EXAMPLE 4

Inhibition of AGE-Photosensitization of Human Skin Cells by d-Penicillamine

Figure 16:
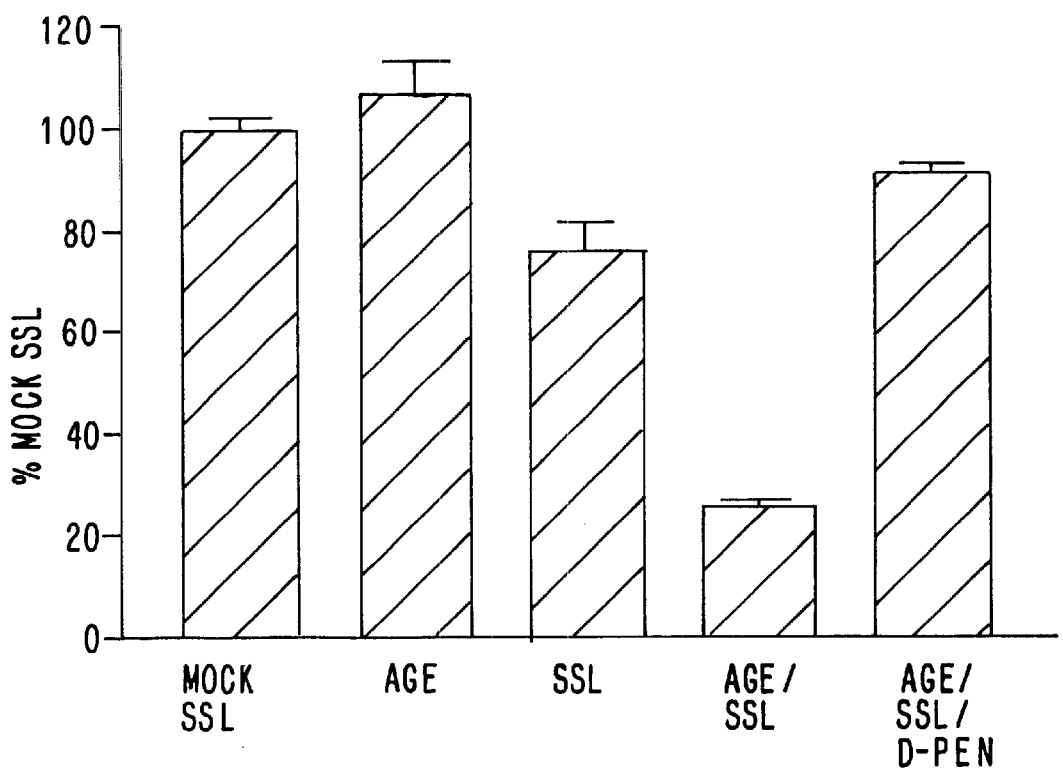
FIG. 16 shows the results of Example 4.

Human HaCat keratinocytes growing on 35 mm dishes were exposed to solar simulated light (1.2 kJ/m² UVB and 23 kJ/m² UVA) in the presence or absence of AGE-BSA as a model of a protein with advanced glycation endproducts. Control populations were treated in exactly the same way as described above, but were not exposed to solar simulated light (SSL). Exposure of HaCat cells to SSL effected a 20% growth inhibition compared to cells which were not exposed (see below). However, cells exposed to SSL in the presence of 10 mg/mL AGE-BSA were growth inhibited by 80%, showing that AGE-BSA is a photosensitizer, effecting a 4 fold increase in growth inhibition as compared to SSL alone. Exposure to 10 mg/mL AGE-BSA alone in the absence of SSL had no effect on cell growth. Results are shown in FIG. 16.

Hence, AGE-BSA is completely non-toxic in the absence of SSL, but can exert significant toxicity when photoactivated by SSL. Furthermore, 10 mM D-penicillamine, previously shown to exert no toxic effects on HaCat cells, completely reversed the photosensitization effect. Therefore, D-penicillamine is an effective inhibitor of photosensitization exerted by glycated proteins and related age-pigments in human skin.

EXAMPLE 5

Human skin consists of keratinocytes and fibroblasts growing in a collagen matrix. Skin aging, as well as certain pathological conditions, e.g. diabetes, leads to the collagen matrix becoming glycated.

Figure 17:
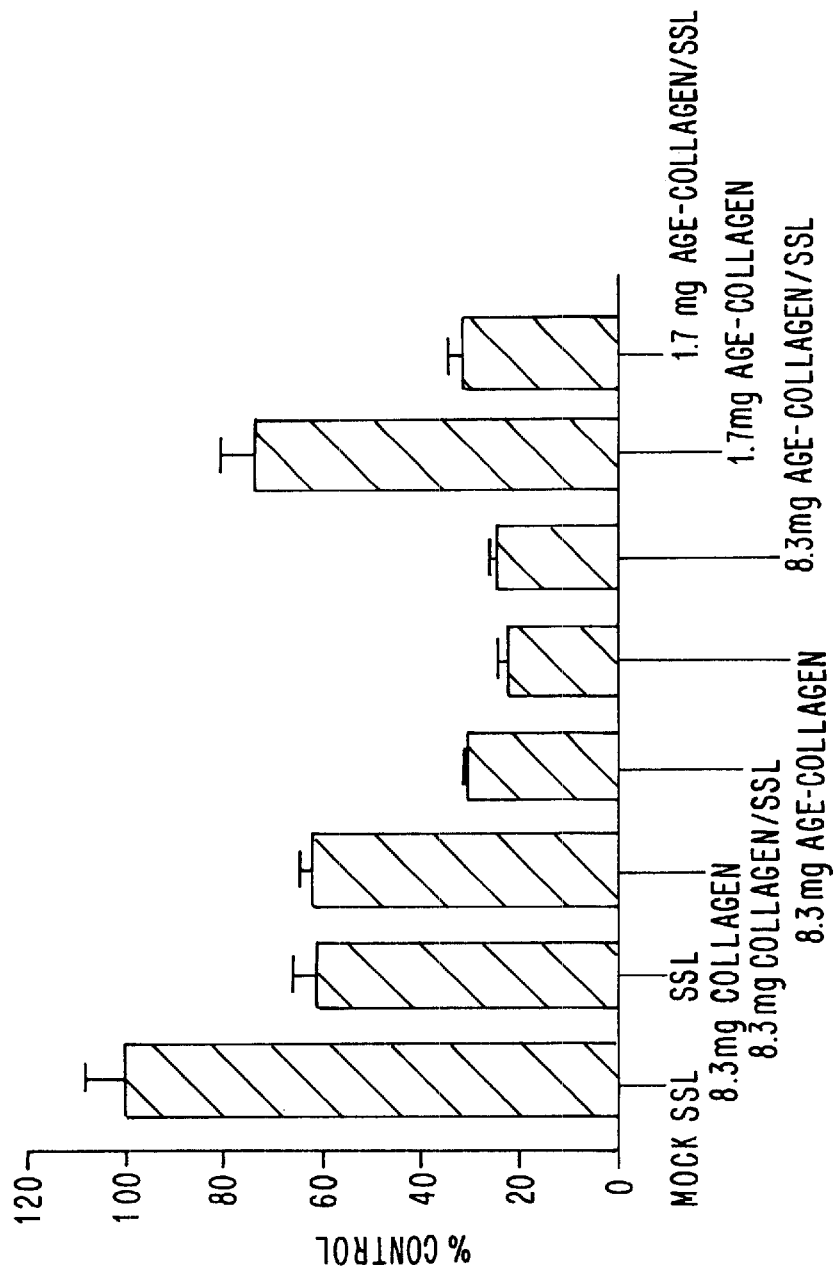
FIG. 17 shows the results of Example 5.

The experiment described above was repeated in exactly the same way, but CF-3 fibroblasts and glycated collagen (AGE-collagen) was used (see above). Exposure to 2 mg/mL AGE-collagen with SSL also showed a photosensitization effect. It is therefore feasible that D-penicillamine can be used topically to inhibit photosensitization effects in human skin relevant for the prevention of skin photoaging and skin photocarcinogenesis. Result are shown in FIG. 17.

The results from the above experiments show that α-amino-β,β-mercapto-β,β-dimethyl-ethane derivatives (pharmacophore), especially penicillamines, are useful in prevention of AGE-related damage to the skin of a subject, particularly mammals such as humans. The results also show that these compounds provide effective protection of skin cells and genetic toxicity induced by photoaging. This can be accomplished, e.g., by systemic delivery through oral, parenteral, e.g., intravenous, topical or other suitable delivery means. A sufficient dose of the agent will be given to produce the desired effect in the subject, which can be any animal, mammal, reptile, etc. The dose will vary upon a variety of factors known to those skilled in the art, e.g., weight, desired therapeutic endpoint, weight of the subject, etc.

TABLE 1

Screening of inhibitors of nonoxidative advanced glycation:
AGE-fluorescence on 96 well-microtiter plate

| sample | AGE-fluorescence[1] (day 0) | AGE-fluorescence[1] (day 5) | AGE-BSA test[1] |
|---|---|---|---|
| histone H1 blank | 1.1 (0.0) | 1.5 (0.2) | |
| complete reaction | | | |
| under argon (+5 mM DTPA) | 1.1 (0.1) | 23 (1.1) | 32 |
| under air + compound | 1.1 (0.1) | 21 (0.9) | 30 |
| Aminoguanidine 1 mM | 1.2 (0.1) | 4.3 (0.2) | |
| 5 mM | 1.2 (0.1) | 2.0 (0.0) | |
| 10 mM | 1.3 (0.1) | 1.8 (0.0) | 10 |
| Rutin 200 μM | 1.0 (0.0) | 3.0 (0.1) | 5.7 |
| NADH 5 mM | 52 (0.3) | 31 (0.0) | |
| L-Cys-Gly 1 mM | 1.3 (0.3) | 17 (0.0) | |
| 5 mM | 1.2 (0.2) | 26 (0.4) | |
| 10 mM | 1.2 (0.1) | 40 (0.0) | |
| GSH 1 mM | 1.3 (0.0) | 19 (0.3) | |
| 5 mM | 1.1 (0.3) | 17 (0.3) | |
| 10 mM | 1.1 (0.0) | 14 (0.5) | |
| L-Cys 1 mM | 1.2 (0.1) | 14 (0.3) | |
| 5 mM | 1.1 (0.1) | 11 (0.2) | |
| 10 mM | 1.2 (0.1) | 9.0 (0.2) | |
| L-Cys-OMe 1 mM | 1.2 (0.1) | 15 (0.1) | |
| 5 mM | 1.3 (0.1) | 12 (0.8) | |
| 10 mM | 1.2 (0.1) | 9.0 (0.2) | |
| NAC 1 mM | 1.2 (0.2) | 11 (0.6) | |
| 5 mM | 1.0 (0.1) | 10 (0.4) | |
| 10 mM | 1.1 (0.1) | 9.4 (0.6) | |
| D,L-Homocysteine 1 mM | 1.3 (0.0) | 16 (1.1) | |
| 5 mM | 1.2 (0.2) | 22 (0.1) | |
| 10 mM | 1.1 (0.1) | 27 (1.7) | |
| Cysteamine 1 mM | 1.0 (0.1) | 10 (0.6) | |
| 5 mM | 1.1 (0.1) | 9.0 (0.7) | |
| 10 mM | 1.2 (0.2) | 6.0 (0.3) | |
| D,L-Penicillamine 1 mM | 1.1 (0.2) | 13 (0.0) | |
| 5 mM | 1.1 (0.1) | 2.7 (0.0) | |
| 10 mM | 1.1 (0.1) | 1.7 (0.0) | 15 |
| D-Penicillamine 1 mM | 1.2 (0.0) | 11 (0.6) | |
| 5 mM | 1.1 (0.1) | 2.9 (0.3) | |
| 10 mM | 1.1 (0.0) | 1.4 (0.1) | 12 |
| 2-Thiobarbituric acid 1 mM | 1.1 (0.1) | 12 (0.4) | |
| 5 mM | 1.2 (0.1) | 5.3 (0.4) | |
| 10 mM | 1.3 (0.1) | 2.3 (0.0) | 12 |
| L-Ergothioneine 1 mM | 1.0 (0.1) | 13 (0.0) | |
| 5 mM | 1.2 (0.0) | 9.3 (0.2) | |
| 10 mM | 1.2 (0.1) | 7.4 (0.1) | |
| Thiourea 1 mM | 1.1 (0.1) | 18 (0.1) | |
| 5 mM | 1.1 (0.1) | 15 (0.0) | |
| 10 mM | 1.1 (0.2) | 11 (0.3) | |

[1]Fluorescence in relative units (± SEM, n = 2)

Other embodiments of the invention will be readily apparent to those skilled in the art and are meant to be within the scope of the claims appended hereto.

All cited references are hereby incorporated by reference.

We claim:

1. A method for inhibiting production of advanced glycosylation end products in a subject comprising administering to the subject a therapeutically effective amount of a pharmaceutical compound having the formula $(R1)(NH_2)CHC(R2)(R3)(SH)$ wherein R1 is H; and R2 and R3 are independently H and CH3.

2. A method for inhibiting production of advanced glycosylation end products in a subject comprising administering to the subject a therapeutically effective amount of at least one compound selected from the group consisting of 3,3-dimethylcysteine-disulfide and N,S-isopropylidene-3,3-dimethylcysteine.

* * * * *